United States Patent
Hackenberger et al.

(10) Patent No.: US 8,575,282 B2
(45) Date of Patent: Nov. 5, 2013

(54) COMPOUND MODIFIED BY A PHOSPHORAMIDATE AND/OR PHOSPHONAMIDE GROUP AND USE THEREOF

(75) Inventors: Christian Hackenberger, Berlin (DE); Giuseppe Del Signore, Nijmegen (NL); Remigiusz Serwa, Berlin (DE); Ina Wilkening, Berlin (DE); Robert Vallee, Berlin (DE)

(73) Assignee: Freie Universitaet Berlin, Berlin (DE)

( * ) Notice: Subject to any disclaimer, the term of this patent is extended or adjusted under 35 U.S.C. 154(b) by 0 days.

(21) Appl. No.: 13/255,864

(22) PCT Filed: Mar. 9, 2010

(86) PCT No.: PCT/EP2010/052968
§ 371 (c)(1),
(2), (4) Date: Sep. 9, 2011

(87) PCT Pub. No.: WO2010/102997
PCT Pub. Date: Sep. 16, 2010

(65) Prior Publication Data
US 2012/0065344 A1  Mar. 15, 2012

(30) Foreign Application Priority Data
Mar. 9, 2009  (DE) .................. 10 2009 012 640

(51) Int. Cl.
C08G 79/02  (2006.01)
(52) U.S. Cl.
USPC ......... 525/538; 525/54.1; 525/54.2; 525/540; 530/330; 530/408; 530/410; 536/22.1; 536/26.1; 977/774; 977/773; 977/896; 977/810; 977/902
(58) Field of Classification Search
USPC ........ 525/54.1, 54.2, 538, 540; 530/330, 410, 530/408; 536/22.1, 26.1; 977/774, 773, 977/896, 810, 902
See application file for complete search history.

(56) References Cited

U.S. PATENT DOCUMENTS

| 5,039,796 | A | | 8/1991 | Engels et al. |
| 5,519,126 | A | | 5/1996 | Hecht |
| 5,650,234 | A | * | 7/1997 | Dolence et al. ............... 428/447 |
| 6,043,094 | A | * | 3/2000 | Martin et al. ................. 435/458 |
| 2002/0016003 | A1 | | 2/2002 | Saxon et al. |
| 2006/0079486 | A1 | | 4/2006 | Zalipsky |
| 2008/0075661 | A1 | | 3/2008 | Robillard et al. |
| 2008/0081782 | A1 | | 4/2008 | Li et al. |
| 2010/0093990 | A1 | | 4/2010 | Heindl |

FOREIGN PATENT DOCUMENTS

| DE | 3507881 A1 | 9/1986 |
| DE | 60120650 T2 | 5/2007 |
| WO | WO 01/68565 A2 | 9/2001 |
| WO | WO 2006/038184 A2 | 4/2006 |
| WO | WO 2007/110624 A2 | 10/2007 |
| WO | WO 2008/128686 A1 | 10/2008 |

OTHER PUBLICATIONS

Robins, R.K., et al.; Journal of Heterocyclic Chemistry, 1993, vol. 30, p. 1181-1189.*
Ugorski, M., et al.; Acta Biochimica Polonica, 2002, vol. 49, p. 303-311.*
Faham, S., et al.; Science, Feb. 23, 1996, vol. 271, p. 1116-1120.*
R. Serwa et al.: Site-specific PEGylation of proteins by a Staudinger-phosphite reaction Chemical Science 2010, DOI: 10.1039/cOsc00324g, 596-602.
E. Saxon et al.: Cell Surface Engineering by a Modified Staudinger Reaction Science 2000, 287, 2007-2010.
C.P.R. Hackenberger et al.: Chemoselective Labeling of Engineered Fucosylated Glycoproteins ChemBioChem 2007 8, DOI: 10.1002/cbic.200700417, 1763-1765.
H. Staudinger et al.: Über neue organische Phosphorverbindungen III. Phosphinmethylenderivate und Phosphinimine Helv. Chim. Acta 1919, 2, 635-646.
M. Köhn et al.: The Staudinger Ligation—A Gift to Chemical Biology Angew. Chem. Int. Ed. 2004, 43, DOI: 10.1002/anie.200401744, 3106-3116.
S. Bräse et al.: Organic Azides: An Exploding Diversity of a Unique Class of Compounds Angew. Chem. Int. Ed. 2005, 44, DOI: 10.1002/anie.200400657, 5188-5240.
N.J. Agard et al.: A Comparative Study of Bioorthogonal Reactions with Azides ACS Chem. Biol. 2006, 1, 644-648.
R.L. Letsinger et al.: Selectivity in Binding a Phenanthridinium-Dinucleotide Derivative to Homopolynucleotides J. Am. Chem. Soc. 1981, 103, 7394-7396.
C.P.R. Hackenberger et al.: Chemoselective Ligation and Modification Strategies for Peptides and Proteins Angew. Chem. Int. Ed. 2008, 47, DOI: 10.1002/anie.200801313, 10030-10074.
I. Wilkening et al.: Synthesis of N,N-disubstituted phosphoramidates via a Lewis acid-catalyzed phosphorimidate rearrangement ChemComm. 2008, DOI: 10.1039/b802030b, 2932-2934.
R. Serwa et al.: Phosphoramidate-peptide synthesis by solution- and solid-phase Staudinger-phosphite reactions J. Pept. Sci. 2010, DOI 10.1002/psc.1236, 563-567.
D. Jaradat et al.: Solid-Phase Synthesis of Phosphoramidate-Linked Glycopeptides J. Org. Chem. 2010, 26, DOI: 10.1002/ejoc.201000627, 5004-5009.
Serwa R. et al.: Chemoselective Staudinger-Phosphite Reaction of Azides for the Phosphorylation of Proteins Angewandte Chemie, vol. 48, No. 44, pp. 8234-8239, 2009.

(Continued)

*Primary Examiner* — Robert Jones, Jr.
(74) *Attorney, Agent, or Firm* — Maschoff Brennan

(57) ABSTRACT

A modified compound that has at least one further functional group, in particular a bio- or macromolecule, comprising at least one x-fold (x≥1) chemoselectively incorporated phosphoramidate group of general formula (I), NPO(OR$^1$)(OR$^{1'}$), and/or at least one x-fold (x≥1) chemoselectively incorporated phosphonamide group of general formula (Ia), NPO(R$^1$)(OR$^{1'}$). R$^1$ and R$^{1'}$ is selected from the group containing glycerol, polyglycerol, PEG polymers of the general empirical formula $C_{2n}H_{4n+2}O_{n+1}$ with n≥1, $C_n$-alkyl chains with n≥1; functionalized $C_n$-alkyl chains with n≥1, aryls, heteroaryl, silyl, lipids, fluorophores, saccharides, peptides, crown ethers, or a linker, which links the aforementioned groups. R$^1$ and R$^{1'}$ can be identical to or different from one another.

12 Claims, 13 Drawing Sheets

(56) References Cited

OTHER PUBLICATIONS

Böhrsch V. et al.: Site-specific funktionalisation of proteins by a Staudinger-type reaction using unsymmetrical phosphites Chemical Communications, vol. 46, No. 18, pp. 3176-3178, 2010.

Camp N.P. et al.: Synthesis of stereochemically defined phosphonamidate-containing peptides: Inhibitors fort he HIV-1 proteinase Bioorganic & Medicial Chemistry Letters, vol. 2, No. 9, pp. 1047-1052, 1992.

Morr M. et al.: Cyclic peptide-nucleotide hybrids (cPNH) with phosphoramidate bonds Tetrahedron, Elsevier Science Ltd. vol. 55, No. 10, pp. 2985-2996, 1999.

Sikora D. et al.: O-Ethyl 1-azidoalkylphosphonic acids-versatile reagents for the synthesis fo protected phosphonamidate peptides Tetrahedron, Elsevier Science Ltd. vol. 57, No. 8, pp. 1619-1625, 2001.

\* cited by examiner a)

```
001 MSEQNNTEMT  FQIQRIYTKD  ISFEAPNAPH  VFQKDWQPEV  KLDLDTASSQ
051 LADDVYEVVL  RVTVTASLGE  ETAFLCEVQQ  GGIFSIAGIE  GTQMAHCLGA
101 YCPNILFPYA  RECITSMVSR  GTFPQLNLAP  VNFDALFMNY  LQQQAGEGTE
151 EHQDAXGHHH  HHH
``` b)

| GluC: | control  | - HQDAXGHHHHHH | = 1349,55 + X |
|       | reaction | - HQDAYGHHHHHH | = 1349,55 + Y |
| AspN: | control  | - DAXGHHHHHH   | = 1084,46 + X |
|       | reaction | - DAYGHHHHHH   | = 1084,46 + Y |

Fig. 3B

DMSO/buffer ph 8.2
25° detection of luminescence
StAv-HRP + H₂O₂ + luminol lane 1: Marker
lane 2: SecB-N₃
  +Biotin-OP(OMe)₂
  in buffer/DMSO 1:1
lane 3: SecB-N₃
  +Biotin-OP(OMe)₂
  in buffer/DMSO 4:1
lane 4: SecB-N₃
  +Biotin-OH
lane 5: SecB-N₃

MALDI-MS:

```
                          SEQUENCE LISTING

<160> NUMBER OF SEQ ID NOS: 2

<210> SEQ ID NO 1
<211> LENGTH: 163
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (156)..(156)
<223> OTHER INFORMATION: Xaa is p-Amino-Phe

<400> SEQUENCE: 1

Met Ser Glu Gln Asn Asn Thr Glu Met Thr Phe Gln Ile Gln Arg Ile
1               5                   10                  15

Tyr Thr Lys Asp Ile Ser Phe Glu Ala Pro Asn Ala Pro His Val Phe
            20                  25                  30

Gln Lys Asp Trp Gln Pro Glu Val Lys Leu Asp Leu Asp Thr Ala Ser
        35                  40                  45

Ser Gln Leu Ala Asp Asp Val Tyr Glu Val Val Leu Arg Val Thr Val
    50                  55                  60

Thr Ala Ser Leu Gly Glu Glu Thr Ala Phe Leu Cys Glu Val Gln Gln
65                  70                  75                  80

Gly Gly Ile Phe Ser Ile Ala Gly Ile Glu Gly Thr Gln Met Ala His
                85                  90                  95

Cys Leu Gly Ala Tyr Cys Pro Asn Ile Leu Phe Pro Tyr Ala Arg Glu
            100                 105                 110

Cys Ile Thr Ser Met Val Ser Arg Gly Thr Phe Pro Gln Leu Asn Leu
        115                 120                 125

Ala Pro Val Asn Phe Asp Ala Leu Phe Met Asn Tyr Leu Gln Gln Gln
    130                 135                 140

Ala Gly Glu Gly Thr Glu Glu His Gln Asp Ala Xaa Gly His His His
145                 150                 155                 160

His His His

<210> SEQ ID NO 2
<211> LENGTH: 163
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (156)..(156)
<223> OTHER INFORMATION: Xaa is phosphorylated Phe

<400> SEQUENCE: 2

Met Ser Glu Gln Asn Asn Thr Glu Met Thr Phe Gln Ile Gln Arg Ile
1               5                   10                  15

Tyr Thr Lys Asp Ile Ser Phe Glu Ala Pro Asn Ala Pro His Val Phe
            20                  25                  30

Gln Lys Asp Trp Gln Pro Glu Val Lys Leu Asp Leu Asp Thr Ala Ser
        35                  40                  45

Ser Gln Leu Ala Asp Asp Val Tyr Glu Val Val Leu Arg Val Thr Val
    50                  55                  60
```

```
Thr Ala Ser Leu Gly Glu Glu Thr Ala Phe Leu Cys Glu Val Gln Gln
 65              70                  75                  80

Gly Gly Ile Phe Ser Ile Ala Gly Ile Glu Gly Thr Gln Met Ala His
             85                  90                  95

Cys Leu Gly Ala Tyr Cys Pro Asn Ile Leu Phe Pro Tyr Ala Arg Glu
            100                 105                 110

Cys Ile Thr Ser Met Val Ser Arg Gly Thr Phe Pro Gln Leu Asn Leu
        115                 120                 125

Ala Pro Val Asn Phe Asp Ala Leu Phe Met Asn Tyr Leu Gln Gln Gln
        130                 135             140

Ala Gly Glu Gly Thr Glu Glu His Gln Asp Ala Xaa Gly His His His
145             150                 155                 160

His His His
```

COMPOUND MODIFIED BY A PHOSPHORAMIDATE AND/OR PHOSPHONAMIDE GROUP AND USE THEREOF

CROSS-REFERENCE TO A RELATED APPLICATION

This application is a National Phase Patent Application of International Patent Application Number PCT/EP2010/052968, filed on Mar. 9, 2010, which claims priority of German Patent Application Number 10 2009 012 640.6, filed on Mar. 9, 2009.

BACKGROUND

The present invention relates to a modified compound, a method of chemoselective phosphorylation and a method of site-specific immobilization.

Chemoselective reactions have become an important tool in chemical research and in the biosciences, as they allow functional modules, for example biophysical probes, to be incorporated selectively in complex biomolecules. The essential element of chemoselective reactions is the selective transformation of a specific functionality within a complex biomolecule.

Various approaches are known for the selective functionalization of biomolecules, which are mainly included in the group of macromolecules. For example, naturally occurring functional groups such as thiols or phenols can be selectively modified, but site-specific labeling is not possible, as other thiols or phenols can also react.

Another approach comprises introducing nonnatural functionalities into biological molecules. Thus, it is possible, by established biochemical methods, to introduce azides into biological macromolecules, which are then available for further reaction. This method makes a site-specific modification possible, as the nonnatural functional group can be functionalized selectively by a chemoselective reaction.

Azide groups can for example be reacted chemoselectively with molecules with multiple bonds in the presence of copper (I) catalysts (Click Chemistry), but the use of toxic copper(I) catalysts is a disadvantage for application in living systems.

Another approach is described in WO 2001/068565 A2 or DE 601 20 650. Here, a chemoselective ligation reaction is carried out using phosphines for linking two reactants in mild reaction conditions (Staudinger ligation). This ligation reaction is based on the Staudinger reaction, in which an azide reacts chemoselectively with a phosphine to an iminophosphorane. To avoid hydrolysis of the iminophosphorane, this reaction can be manipulated so that an internal electrophilic substituent of the phosphine captures the resultant iminophosphorane, leading to formation of an amide bond in the end product. Drawbacks in this process are the slow reaction rate, the competitive iminophosphorane hydrolysis that still occurs, the sensitivity of phosphines to oxidation and the fact that the phosphines with the internal electrophilic substituent must be produced by a multistage process.

SUMMARY

The invention is therefore based on the problem of providing a chemoselective method of production of modified compounds, in particular of modified bio- or macromolecules, which does not have the aforementioned drawbacks.

According to an exemplary embodiment of the invention, the modified compound that has at least one further functional group is characterized by at least one x-fold (x≥1) chemoselectively incorporated phosphoramidate group of general formula (I)

and/or at least one x-fold (x≥1) chemoselectively incorporated phosphonamide group of general formula (Ia)

wherein $R^1$ and $R^{1'}$ is selected from the group containing
glycerol, polyglycerol,
PEG polymers of the general empirical formula $C_{2n}H_{4n+2}O_{n+1}$ with $n \geq 1$
$C_n$-alkyl chains with $n \geq 1$, preferably methyl, ethyl or butyl,
functionalized $C_n$-alkyl chains with $n \geq 1$, preferably —CH$_2$—(NO$_2$)Ar, coumarin, enzymatically cleavable esters, 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, 1-chloroethyl, 2-chloroethyl, 1-bromoethyl, 2-bromoethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminoethyl, 1-aminoethyl, N-benzoyl-2-aminoethyl, N-acetyl-2-aminoethyl, N-benzoyl-1-aminoethyl or N-acetyl-1-aminoethyl,
aryls, preferably phenyl, benzyl, naphthyl, or anthryl,
heteroaryl, preferably pyridinyl, pyrimidinyl, pyrazinyl, pyridazinyl, pyrrolo, furano, oxazolo, isooxazolo, phthalimido, thioazolo
silyl, preferably trialkylsilyl,
lipids, preferably hydrophobic fatty acid moieties, terpenes such as palmitoyl or farnesyl,
fluorophores, preferably fluorescein, Bodipy dyes or FRET labels
isotope labels, preferably radioactive isotopes, isotopes for NMR techniques or imaging techniques,
saccharides, in particular oligosaccharides,
peptides,
crown ethers, or
a linker, which links the aforementioned groups, and wherein $R^1$ and $R^{1'}$ can be identical to or different from one another. The number n of incorporated phosphoramidate and/or phosphonic acid groups can be established in a definite, targeted manner, i.e. chemoselectively, based on the method of synthesis applied according to the Staudinger reaction starting from functionalized azides. Therefore no arbitrary and non-site-specific modification of bio- or macromolecules occurs.

Based on the conditions of chemoselective synthesis, the phosphoramidate and/or phosphonic acid groups are preferably bound to aromatic and/or alkyl moieties of the bio- or macromolecules. Thus, the chemoselective modification of proteins and/or peptides is preferably carried out using p-azidophenylalanine or various alkylazido amino acids, e.g. azidohomoalanine. Therefore the phosphoramidate and/or phosphonic acid groups in proteins in particular are bound to a phenylalanine and/or homoalanine moiety. Thus, alkyl or aryl azides are preferably used for the modification of macromolecules.

The aforementioned groups $R^1$, $R^{1'}$ and $R^{1''}$ can of course be of substituted or unsubstituted form, wherein possible substituents are familiar to a person skilled in the art. Preferably used groups are fluorophores, such as fluorescein, Bodipy dyes or FRET labels, isotope labels, saccharides, nitrobenzyl, PEGs, coumarin, biotin. The use of fluorophores, PEGs, biotin and/or isotope labels is especially preferred.

Preferably, therefore, a functional group is coupled to the higher-molecular compounds via the phosphoramidate group and/or the phosphonamide group.

Preferably, the further functional group of the modified compound, in particular of the bio- or macromolecule, is in protected or unprotected form. Especially preferred functional groups are selected from a group containing —OH, —$NH_2$, —SH, —$CO_2H$, —$CONH_2$ and disulfides, guanidines such as —$NHCNHNH_2$ in arginine, imidazoles as in histidine, indoles as in tryptophan. Additionally, alkenes and/or alkynes can be present in macromolecules as further functional groups.

The number x of incorporated phosphoramidate and/or phosphonic acid groups is preferably between 1 and 100, especially preferably between 1 and 30 and quite especially preferably between 1 and 15.

The compounds according to the invention are prepared in a modified Staudinger reaction, wherein the compounds are reacted at a pH between 6 and 10, preferably at pH 7 to 8, at temperatures between 18 and 45° C., preferably at room temperature, for a period of up to 48 h, preferably 12 h with a phosphite of general formula (II)

$$P(OR^1)(OR^{1'})(OR^{1''}) \quad (II),$$

and/or a phosphonite of general formula (IIa)

$$PR^1(OR^{1'})(OR^{1''}) \quad (IIa)$$

wherein $R^1$, $R^{1'}$ and $R^{1''}$ have the above meaning of $R^1$ and $R^{1'}$, and can be identical to or different from one another.

Reactions can, however, also be carried out in or by adding other solvents, preferably DMF, DMSO, THF, provided the compounds to be modified tolerate the solvent that is added.

The chemoselective method described here makes it possible to carry out the coupling reaction in mild reaction conditions, e.g. in aqueous solution at room temperature. The phosphite and phosphonite components can easily be synthesized and are not sensitive to oxidation. Furthermore, the chemoselective reaction between azides and phosphites and/or phosphonites does not require the addition of toxic Cu(I) metal catalysts, as when using Click Chemistry for example. Application in an intracellular reaction is therefore possible.

In one exemplary embodiment of the present invention, the modified phosphoramidate group of formula (I) incorporated in the bio- or macromolecule can be transformed to a free phosphoramide group of general formula (III)

$$-NPO(OH)_2 \quad (III)$$

by photolysis and/or hydrolysis. This makes it possible to produce analogues of phosphorylated proteins, which, just like phosphorylated proteins, can be recognized e.g. by antibodies or kinases.

Similarly, the incorporated modified phosphonamide group of formula (Ia) can be transformed to a free phosphonamide group of general formula (IIIa)

$$-NP(O)R^1(OH) \quad (IIIa)$$

by photolysis and/or hydrolysis.

Thus, it is possible, by splitting-off photolabile groups such as o-nitrobenzyl or coumarins, to convert the compounds to compounds of general formula (III) or (IIIa).

In another exemplary embodiment, the compounds according to the invention can be immobilized, via the incorporated phosphoramidate/phosphonamide groups, on the surface of a support. Functionalized glass surfaces, microplates, nanoparticles, in particular gold or silica nanoparticles and quantum dots can be used here as supports.

The compounds that are used are preferably selected from the group containing polymers, peptides, proteins, glycans, lipids, polynucleotides, polyketides and/or other natural substances. It is important that the molecules to be modified have at least one azide group, which for example is correspondingly introduced into the molecule during the synthesis process.

The peptides used are preferably peptides with a chain length of greater than 2 amino acids, in particular greater than 6 amino acids. Pharmacologically relevant peptides and hormones, which are to be modified for improving the biological activity or bioavailability, are of particular interest. The hormones and/or peptides can be selected from a group containing growth hormones, stress hormones, steroid hormones, neuropeptides, thyroid hormones, peptide hormones of the gastrointestinal tract and others.

The polymers used can be polyglycerols, in particular PG10 or other polymers bearing an azide group. The polymers used typically have a molecular weight between 1 and 40 kDa.

The modification of physiologically relevant natural substances such as signal peptides, glycolipids or sphingolipids or pharmacologically and biologically relevant proteins, which are important in particular for proteome research and the elucidation of signal transduction processes, is especially advantageous.

An especially interesting group of proteins is the class of proteins that are responsible for the transport of proteins from the interior of the cell across the membrane. A typical representative of this class is the Sec system, comprising e.g. SecB. Kinases involved in signal transduction or in sugar metabolism are also preferred, e.g. glucokinases, phosphofructokinases or protein kinases. Another preferred group of proteins comprises the class of phosphatases, regulatory proteins and/or glycoproteins.

The compounds according to the invention can be used in the pharmaceutical or biotechnology industry as phosphatase or kinase substrates, as marker molecules, as biochemical probes for elucidating biological function, as stabilizing factors against proteolysis through incorporation of PEG or also as pharmaceutically active substances, in particular inhibitors.

Site-specific labeling or functionalization makes possible e.g. a precise analysis of function, in particular in a complex native environment. Moreover, based on immobilization of the modified compounds, use in research into active substances is possible, as small molecules can be tested in a screening technique. Moreover, the phosphoramidate unit itself might also have a biological action, so that use as enzyme inhibitors is possible, in combination with lipids or peptides.

A large area of application is the bioconjugation of PEG polymers. PEG serves as stabilization of the protein against unintentional protein degradation (proteolysis). An alternative, site-specific bioconjugation of PEG is of great interest to industry, as proteins can thus be made bioavailable. The PEGs used preferably have an average molecular weight from 100 to 40 000.

By means of the chemoselective method using phosphite and/or phosphonite, it is possible to produce modified proteins or modified protein analogues, in particular glycoproteins. The method for chemoselective phosphorylation or phosphonylation of compounds comprises the following steps:

a) synthesis and/or functionalization of a compound with at least one azide ($N_3$) group, preferably with an alkyl and/or aryl azide group, and b) reaction of the at least one azide group of the compound with a phosphite of general formula (II) $P(OR^1)(OR^{1'})(OR^{1''})$ with formation of a phosphoramidate group of general formula (I)
$NPO(OR^1)(OR^{1'})$ and/or
with a phosphonite of general formula (IIa) $PR^1(OR^{1'})(OR^{1''})$ with formation of a phosphonamide group of general formula (Ia)
$NPO(R^1)(OR^{1'})$, wherein the moieties $R^1$, $R^{1'}$ and $R^{1''}$ are assigned the above meaning of $R^1$ and $R^{1'}$.

For the present invention, it is important that the azide used has at least one further functional group in the molecule. This is the case with the majority of the bio- or macromolecules that are used and are to be modified. The further functional group can be present in protected or unprotected form. Especially preferred functional groups are selected from a group containing —OH, —$NH_2$, —SH, —$CO_2H$, —$CONH_2$, as well as disulfides, guanidines such as —$NHCNHNH_2$ in arginine, imidazoles as in histidine, indoles as in tryptophan. Additionally, alkenes and/or alkynes can be present in macromolecules as further functional groups.

In a preferred variant, in a further step c) the phosphoramidate group of general formula (I) is converted to a phosphoramide group of general formula (III) —$NPO(OH)_2$ and/or the phosphonamide group of general formula (Ia) is converted to a phosphonamide group of general formula (IIIa) —$PO(R^1)OH$.

The step of liberation of the phosphoramidate and/or phosphonamide group preferably takes place by photolysis and/or hydrolysis.

The reaction of the $N_3$-containing compound with a phosphite of general formula (II) $P(OR^1)(OR^{1'})(OR^{1''})$ and/or a phosphonite of general formula (IIa) $PR^1(OR^{1'})(OR^{1''})$ is preferably carried out at a pH between 6 and 10, preferably at 7 to 8, at temperatures between 18 and 45° C., preferably at room temperature, for a period of up to 48 h, preferably 12 h.

The compounds produced by this method, in particular the phosphorylated proteins, represent analogues of the naturally phosphorylated proteins in particular with phosphorylations on the amino acids Ser, Thr and Tyr and can be recognized e.g. by antibodies, kinases or phosphatases or protein domains, such as $SH_2$ domains.

The chemoselective method can also be applied for site-specific immobilization of compounds on supports. The method of site-specific immobilization of compounds comprises the following steps a) synthesis or functionalization of a compound with at least one azide ($N_3$—) group, preferably with an alkyl and/or aryl azide group, b) coupling of at least one phosphite of general formula (IV) $P(OR^2)(OR^{2'})(OR^{2''})$ and/or at least one phosphonite of general formula (IVa) $PR^2(OR^{2'})(OR^{2''})$ to the surface of at least one support $R^3$, wherein $R^2$, $R^{2'}$ and $R^{2''}$ are selected from the group containing $C_n$-alkyl chains with $n \geq 1$, preferably methyl, ethyl or butyl, functionalized $C_n$-alkyl chains with $n \geq 1$, preferably —$CH_2$—$(NO_2)Ar$, coumarin, enzymatically cleavable esters, 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, 1-chloroethyl, 2-chloroethyl, 1-bromoethyl, 2-bromoethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminoethyl, 1-aminoethyl, N-benzoyl-2-aminoethyl, N-acetyl-2-aminoethyl, N-benzoyl-1-aminoethyl or N-acetyl-1-aminoethyl; aryls, preferably phenyl, benzyl, naphthyl, or anthryl; heteroaryl, preferably pyridinyl, pyrimidinyl, pyrazinyl, pyridazinyl, pyrrolo, furano, oxazolo, isooxazolo, phthalimido, thioazolo; silyl, preferably trialkylsilyl, wherein $R^2$, $R^{2'}$ and $R^{2''}$ can be identical to or different from one another, and c) reaction of the at least one azide group of the compound with the at least one support coupled with the phosphite and/or phosphonite, wherein coupling between the support and the compound takes place via a phosphoramidate and/or phosphonamide group that has formed.

The aforementioned groups can of course be of substituted or unsubstituted form, wherein possible substituents are familiar to a person skilled in the art.

It is also important here that the azide used has at least one further functional group in the molecule. This is the case with the majority of bio- or macromolecules that are used and are to be modified. The further functional group can be present in protected or unprotected form. Especially preferred functional groups are selected from a group containing —OH, —$NH_2$, —SH, —$CO_2H$, —$CONH_2$, as well as disulfides, guanidines such as —$NHCNHNH_2$ in arginine, imidazoles as in histidine, indoles as in tryptophan. In addition, alkenes and/or alkynes can be present in macromolecules as further functional groups.

The preferred support materials used include glass, polymer, silica or nanoparticles. Especially preferred support materials are gold, quantum dots, silica and glass surfaces.

Coupling to the surface of the support material therefore preferably takes place either via a phosphite bond of the general formula $R^3O$—$P(OR^2)(OR^{2'})$ or via a phosphonite bond of the general formula $R^3$—$P(OR^2)(OR^{2'})$, where $R^3$ represents the link to the surface. The site-specific immobilization on various surfaces and supports takes place under similar reaction conditions as described above. In this, a phosphite-functionalized support is treated with a solution of the azido-containing compound, leading to the formation of a covalent linkage between the compound and the support.

With this method, in particular biomolecules can be immobilized for high-throughput techniques (screening). It is then especially important that a site-specific immobilization makes possible a native behavior of the biomolecule in solution, so that the results of the high-throughput technique come very close to the native conditions.

BRIEF DESCRIPTION OF THE DRAWINGS

The invention is explained in more detail below, on the basis of various examples, and referring to the drawings.

FIG. 3B a) shows amino acid sequence of modified SecB (X: p-azido-Phe), b) shows expected amino acid sequences of proteolytic cleavage with GluC or AspN (Y: phosphorylated amino acid).

DETAILED DESCRIPTION

Figure 1:
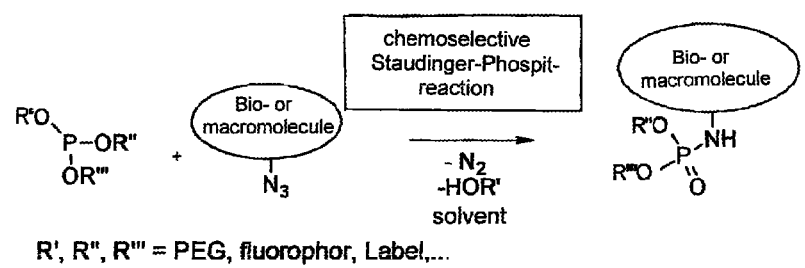
FIG. 1 shows bioconjugation by means of the Staudinger phosphite reaction.

FIG. 1 shows a general scheme for site-specific functionalization of biomolecules by means of the modified Staudinger phosphite reaction. Various modified compounds can be produced, in particular biomolecules (bioconjugates). Thus, bioconjugates can be prepared with PEG polymers, long alkyl chains, fluorophores or isotope labels. The reaction takes place in aqueous solvents in mild reaction conditions.

Example 1

Preparation of Modified Peptides

Figure 2:
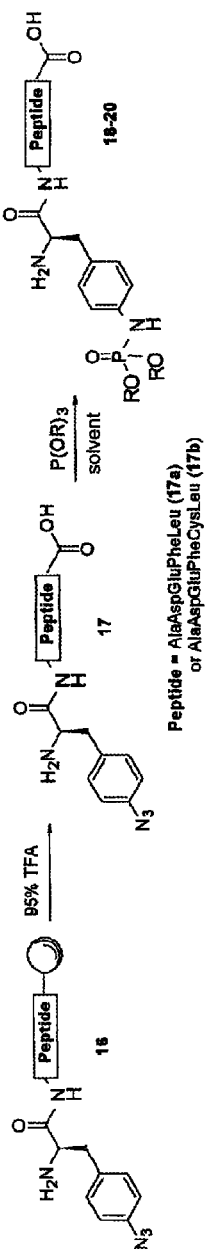
FIG. 2 shows Staudinger phosphite reaction of unprotected phenyl-azido-peptides.

FIG. 2 shows the chemoselective synthesis of peptides AlaAspGluPheLeu 17a and AlaAspGluPheCysLeu 17b modified with phosphoramidate groups (see Table 1). For this, the peptides are synthesized on an ABI443A peptide synthesizer using the standard conditions for amide coupling according to the HBTU/HOBt (Fast-Fmoc protocol) on a Wang resin with Fmoc-p-azido-Phe-OH as last moiety. The peptides are cleaved from the solid phase with 95% TFA and are purified by semi-preparative HPLC.

Then 5-10 equivalents of phosphite (see Table 1) are added to a solution of the azido-peptides (0.2 ml/mg peptide) and the reaction solution is stirred at room temperature for 6 to 24 h. Without further processing, the phosphoramidate-peptides 18-20 are isolated from the reaction solution by preparative HPLC and then lyophilized. The isolated yields are between 39 and 63% (see Table 1).

TABLE 1

Modified peptides

| No. | Peptides | Phosphites | Solvent | Product | Time [h] | Yield [%] |
|---|---|---|---|---|---|---|
| 1 | 17a | P(OBu)$_3$ | DMSO | 18 | 24 | 63 |
| 2 | 17a | P[(OCH$_2$CH$_2$)$_4$OCH$_3$]$_3$ | CH$_3$CN | 19 | 24 | 61 |
| 3 | 17b | P(OEt)$_3$ | DMSO | 20 | 6 | 39 |

Example 2

Figure 3A:
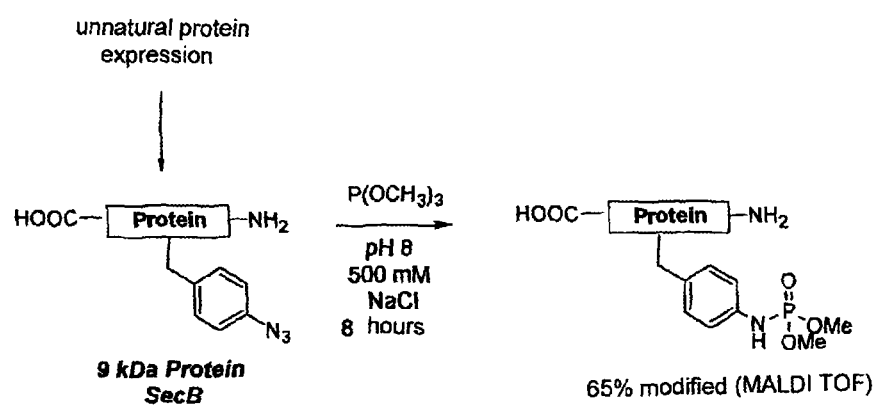
FIG. 3A shows preparation of a phosphoramidate-containing protein by the Staudinger phosphite reaction.

Preparation of Phosphorylated Proteins 2.1. Staudinger Phosphite Reaction of Azidoproteins with Trimethylphosphite The chemoselective functionalization of azidoproteins with a phosphoramidate unit by a Staudinger phosphite reaction was demonstrated by the following experiment. For this, a model protein, SecB, was expressed with a p-azido-Phe amino acid (see FIGS. 3A, B).

Then trimethylphosphite was added to the protein, which had been dissolved in an imidazole buffer at pH 8, and it was shaken overnight at room temperature or at 37° C. Gel electrophoresis and MALDI-MS were used for purification and characterization, and in addition to the two reaction solutions, a solution of the starting protein was also measured for direct comparison.

As the MALDI mass spectrometer can only detect masses from 800 to 3000 (m/z), the protein to be detected was first cleaved proteolytically. As glutamic acid and aspartic acid were each present in the vicinity of the N-terminus of p-azido-Phe, protease cleavage was carried out with GluC or AspN. The sequences to be expected, with the associated mass/charge ratios, are presented in FIG. 3B b). The measured values obtained in the MALDI mass spectrometer are summarized in Table 2.

TABLE 2

MALDI-MS measured values after proteolytic cleavage

| Protease | Theor. mass (without X/Y) | Measured value (with X) | Mass X | Measured value (with Y) | Mass Y |
|---|---|---|---|---|---|
| GluC | 1349.55 | 1511.65 | 162.10 | 1619.64 | 270.09 |
| AspN | 1084.46 | 1246.50 | 162.04 | 1354.52 | 270.06 |

In both measurements, after reaction with trimethylphosphite, in addition to a decrease in intensity of the initial peak, a new peak was seen at higher mass/charge ratio. The mass differences obtained for X and Y correspond, with accuracy to the first decimal place, to the structures of the reduced amine (X) and the phosphorylated amino acid (Y) shown in FIG. 3B. The ratio of the two masses was determined as 35 to 65 (X to Y), so that a 65% modification of the azidoprotein to the phosphoramidate was achieved. Therefore the phosphorylated protein could be detected with certainty, which demonstrates that the reaction also functions in an aqueous environment with very complex proteins.

2.2. Analogues of Phosphorylated Proteins by the Staudinger Phosphite Reaction

Figure 3C:
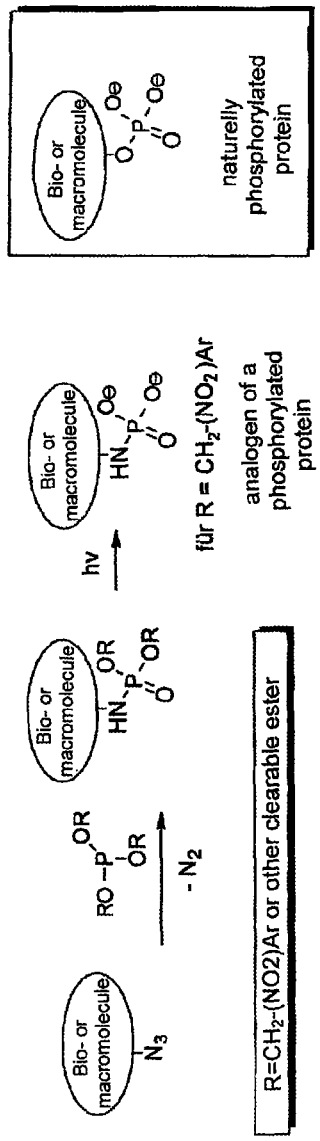
FIG. 3C shows chemoselective phosphorylation of biomolecules.

Based on the results from 2.1., in the next experiment protein-phosphoramidates were prepared, which after photolytic cleavage were transformed to the corresponding phosphate analogues (FIG. 3C).

In a model study, the azido-SecB protein described in 2.1. was also used for this. This was reacted with a water-soluble phosphite bearing three photolabile esters (FIG. 3D).

Figure 3D:
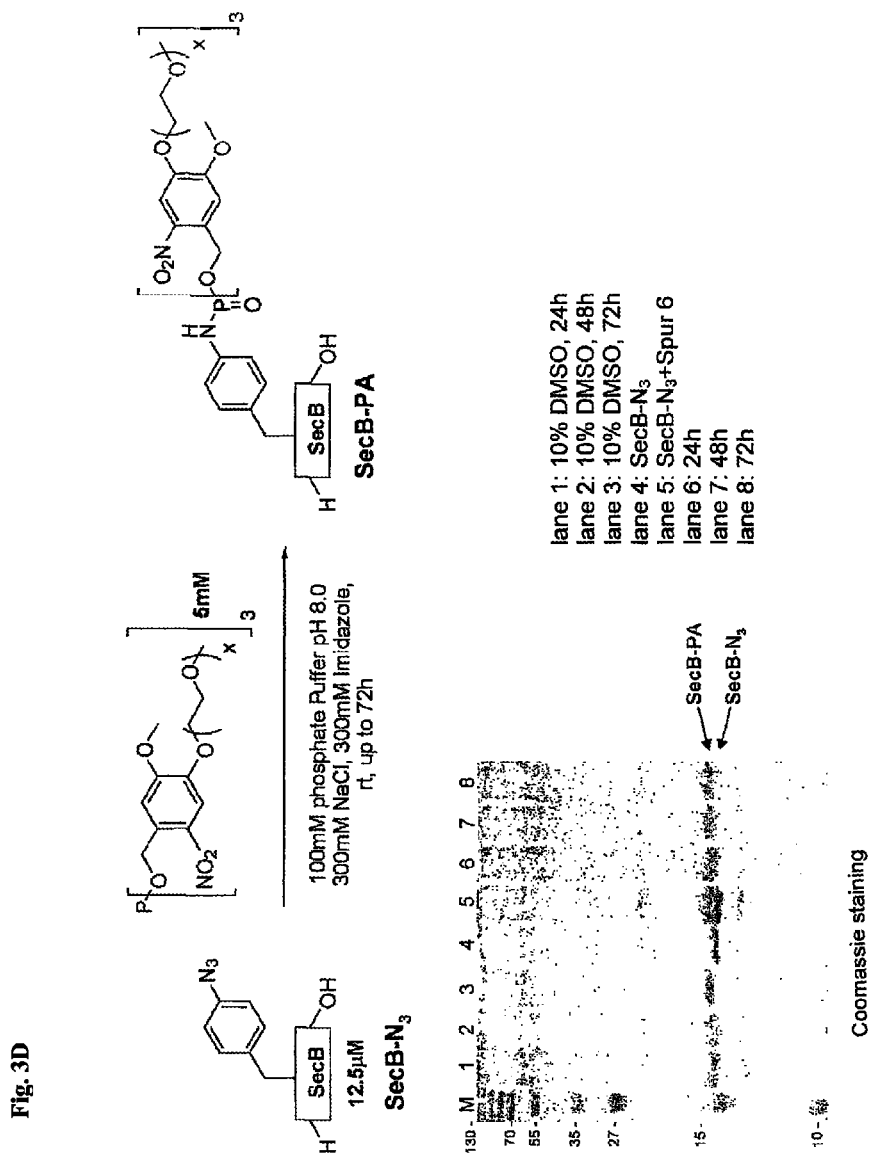
FIG. 3D shows Staudinger phosphite reaction with azido-SecB and gel electrophoresis.

Gel electrophoresis was carried out and showed that after 24 h, both in the pure buffer at pH 8 and with addition of 10% DMSO, the protein had been transformed to the phosphoramidate completely (FIG. 3D).

Figure 3E:
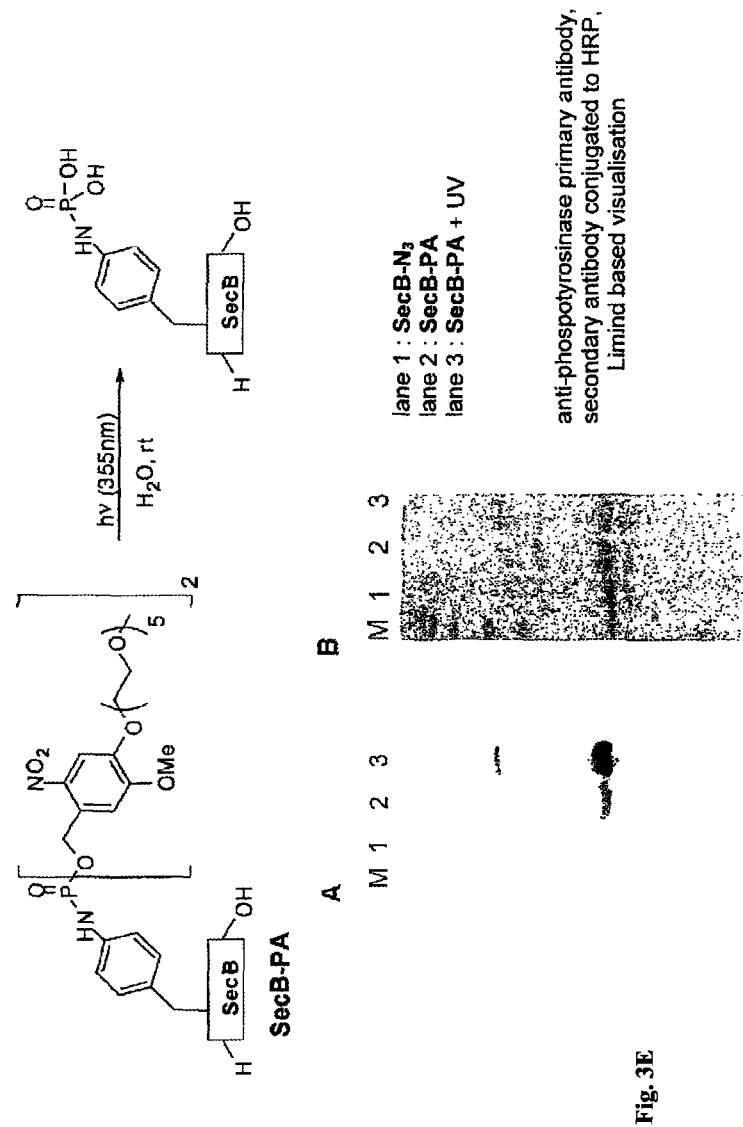
FIG. 3E shows antibody recognition of deprotected phosphoramidates.

Then the phosphoramidate-protein was submitted to photolysis, with irradiation at 355 nm, and was thus transformed to the charged phosphoramidate (FIG. 3E).

Next, recognition reactions were conducted with an antibody that normally recognizes phosphorylated Tyr (anti-phosphotyrosine antibody). It was shown by Western blotting (gel A, FIG. 3E) that after photolysis (lane 3) there is definite recognition of the antibody (deep black coloration). A weak recognition of the protected phosphoramidate (lane 2) can be attributed to partial photolysis by ordinary daylight. In contrast, unmodified azido-SecB (lane 1) is not recognized.

To summarize, it can therefore be stated that the Staudinger phosphite reaction can be used for quantitative preparation of phosphoramidate-containing proteins. These proteins can be converted by suitable ester cleavages to the charged phosphoramidates, which display the same behavior in antibody reactions as naturally phosphorylated proteins (in this case by phosphorylation of a tyrosine).

Example 3

Immobilization of a Compound

Figure 4:
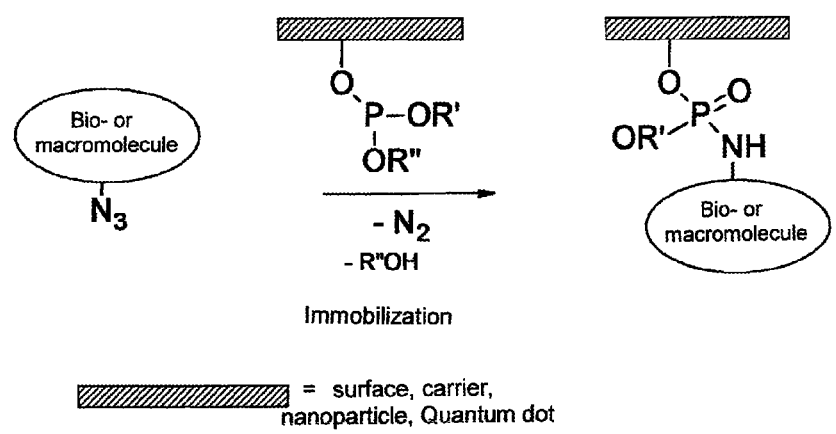
FIG. 4 shows chemoselective protein immobilization by the Staudinger phosphite reaction.

FIG. 4 shows the application of the Staudinger phosphite reaction for site-specific immobilization of compounds. The immobilization takes place on the surface of a support, wherein the support consists of glass, polymer, silica or nanoparticles.

Example 4

Preparation of a Modified Polygycerol

Figure 5:
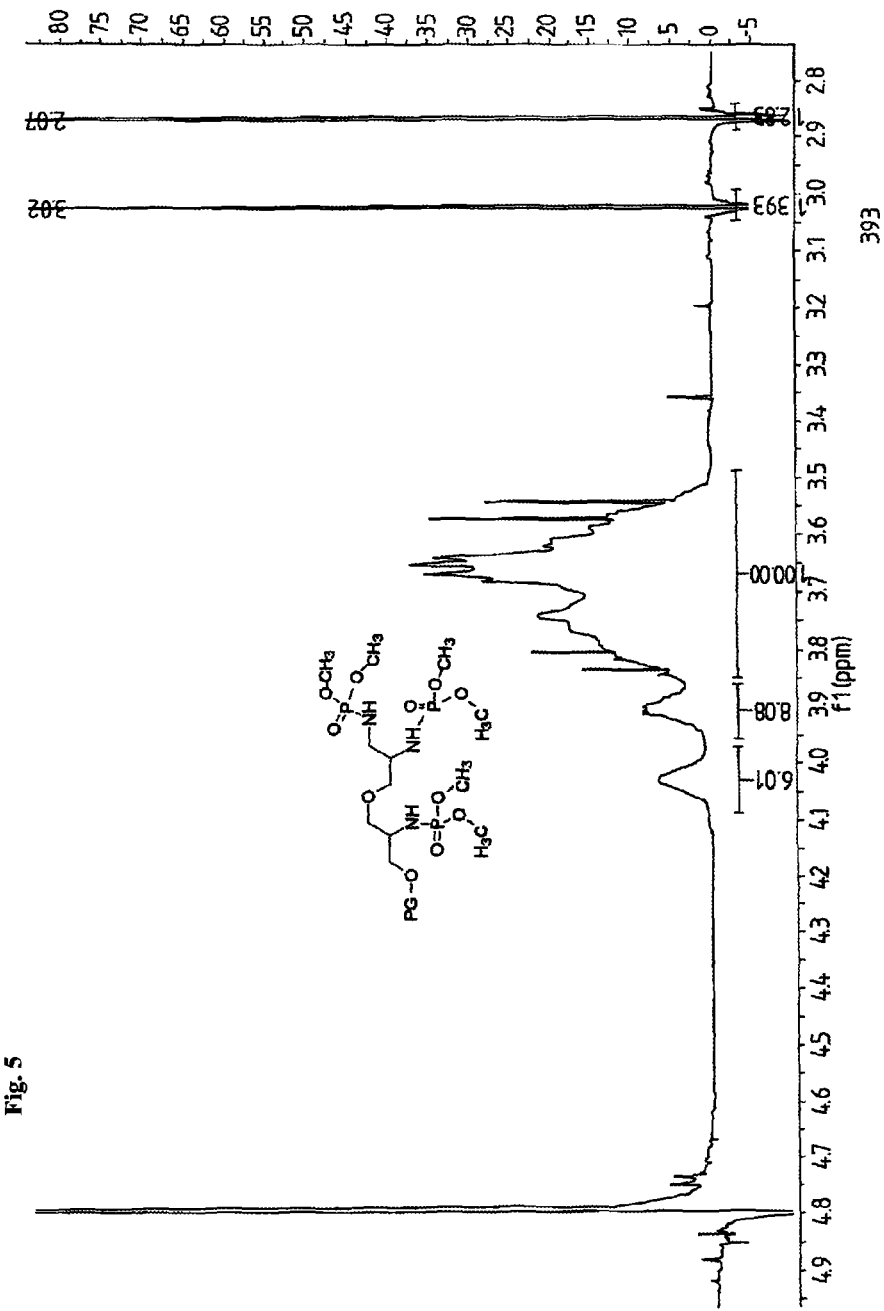
FIG. 5 shows $^1$H-NMR spectrum of a polyglycerol-methylphosphoramidate derivative.

An azide-containing polyglycerol with an average molecular weight of 10 000 g mol-1 (PG10) is reacted with a slight excess of trimethylphosphite, wherein complete reaction to the methylphosphoramidate derivative takes place. The 1H-NMR spectrum (FIG. 5) clearly shows, by doublets with a coupling constant of in each case 12 Hz, that methylphosphoramidate units are present (coupling of methyl protons with phosphorus).

Example 5

Figure 6:
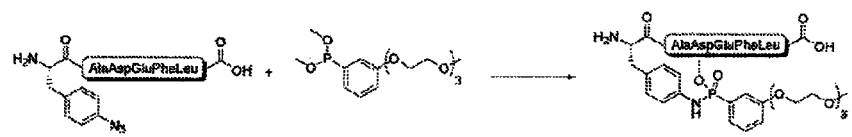
FIG. 6 shows modification of a peptide by means of the reaction according to the invention.

Preparation of Phosphonamide-Containing Peptides by a Staudinger Phosphonite Reaction The chemoselective functionalization of azido-peptides with a phosphonamide unit was demonstrated by the following experiments. An arylphosphonite functionalized with a polyethylene glycol monomethyl ether group, which is accessible synthetically in three stages, was reacted with an azido-peptide bearing an aryl azide, in Tris/HCl buffer at pH=8.2 for 30 minutes (FIG. 6).

TABLE 3

Use of phosphonites for modifying peptides

| Phosphonite (eq.) | Reaction conditions (25° C., 30 min) | Azido-peptide (starting material) [a] | Phosphonamides (product) [a] |
|---|---|---|---|
| $R^2$ = Me (12 eq.) | 1M Tris/HCl buffer (pH 8.2) | 52% | 48% |
| $R^2$ = Me (100 eq.) | 1M Tris/HCl buffer (pH 8.2) 1M Tris/HCl buffer | 43% | 57% |

TABLE 3-continued

Use of phosphonites for modifying peptides

| Phosphonite (eq.) | Reaction conditions (25° C., 30 min) | Azido-peptide (starting material) [a] | Phosphonamides (product) [a] |
|---|---|---|---|
| $R^2$ = Me (100 eq.) | (pH 8.2) w/10% DMSO | <1% | >99% |

[a] Quantification by HPLC-MS

In the subsequent analysis of the reaction mixture by HPLC-MS, apart from the desired phosphonamide-containing peptide, only the unreacted starting material of the azido-peptide could still be detected. Increasing the phosphonite equivalents and admixture of 10% DMSO to improve the solubility and stability of the phosphonite led to almost complete reaction of the azido-peptide to the phosphonamide-containing peptide (see FIG. 6). To summarize, it can therefore be stated that the Staudinger phosphonite reaction can be used for preparing functionalized phosphonamide-containing proteins (Vallée, Hackenberger, unpublished results).

Example 6

PEGylation of Proteins with PEG-Containing Phosphites

Figure 7A:
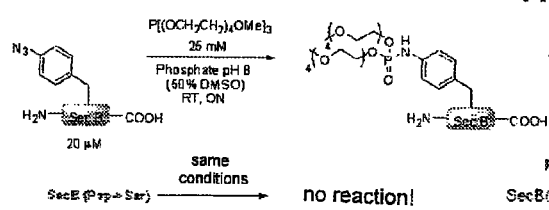
FIGS. 7A-C show modification of a protein with a first PEG molecule by means of the reaction according to the invention.
Figure 7B:
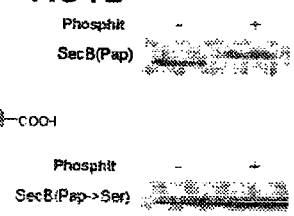

The chemoselective PEGylation of proteins was carried out with the protein SecB, which was obtained by nonnatural protein expression and bears an aryl azide unit (designated here as SecB(Pap), cf. Serwa, Hackenberger et al., Angew. Chem. 2009, 48:8234-8239). Next, the protein was reacted with a symmetrical phosphite (FIG. 7A), in each case bearing four PEG units (Serwa, Hackenberger, et al., unpublished results). The reaction conversion was then investigated by gel electrophoresis (FIG. 7B). It was found that after 14 hours of reaction, the SecB(Pap) was converted quantitatively, as a complete gel shift was observed (FIG. 7, top). In a control experiment, in which the azide unit was replaced with a serine, in contrast no gel shift was observed (FIG. 7B, bottom), which demonstrates the chemoselectivity of the PEGylation.

Figure 7C:
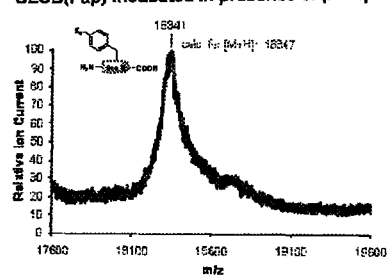
Figure 7C:
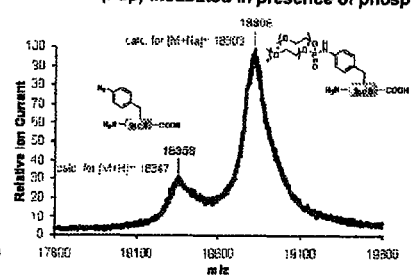

Further evidence for chemoselective phosphorylation was provided by MALDI-MS analysis (FIG. 7C). A covalent mass adduct was only observed for the azidopeptide SecB(Pap) (FIG. 7C, right). The comparative experiment with the azide-free protein did not produce a mass adduct (FIG. 7C, left).

Figure 8A:
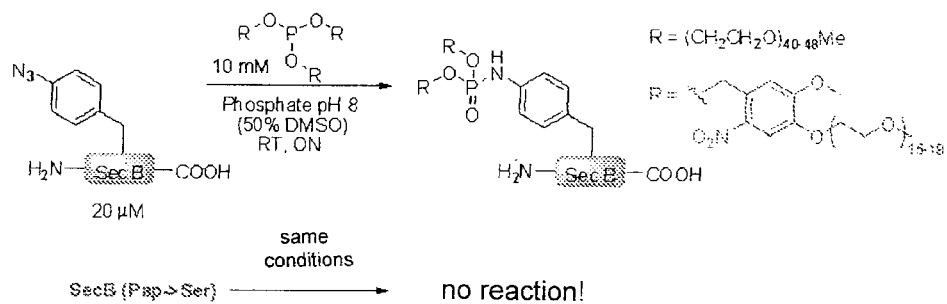
FIGS. 8A-B show modification of a protein with a second PEG molecule by means of the reaction according to the invention.
Figure 8B:
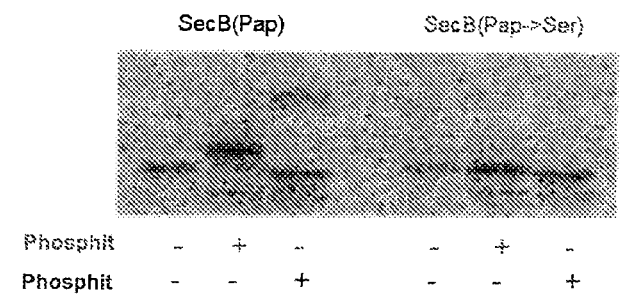

Next, the SecB(Pap) was also reacted with two longer PEG-phosphites with 40-48 PEG units per phosphite substituent or 15-19 units (FIG. 8A). Once again, corresponding chemoselective PEGylations were seen, as verified by gel electrophoresis (FIG. 8B).

To summarize, it can be stated that various PEG-containing phosphites can be used for quantitative reactions of proteins. The reactions proceed and mild conditions (room temperature) in aqueous buffer systems. In addition to the corresponding phosphoramidate-PEG building blocks, a photocleavable PEG-phosphite could also be produced (green phosphite in FIG. 8), for which the PEG unit can be removed again with a laser pulse, which can be promising for switchable protein systems.

Example 7

Biotinylation of Proteins with an Asymmetric Biotin-Phosphite

Figure 9A:
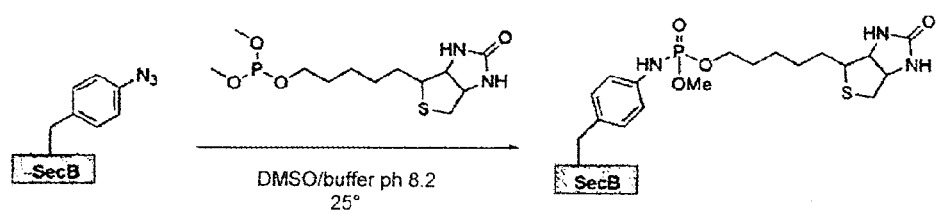
FIG. 9 shows modification of a protein with biotin by means of the reaction according to the invention.
Figure 9B:
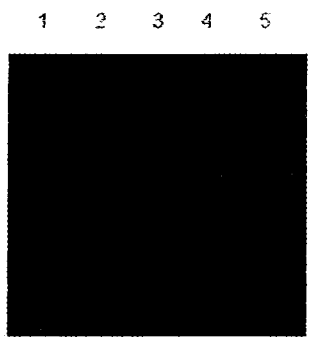
Figure 9C:
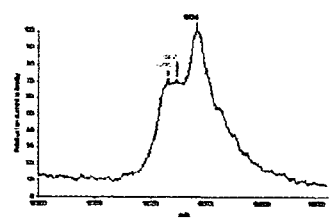

The chemoselective conjugation of biotin-containing phosphites was also demonstrated with the azide-containing model protein SecB. For this, an asymmetric biotin-phosphite was prepared synthetically in 3 stages and was reacted with the azidoprotein in aqueous buffer with DMSO (FIG. 9A). Analysis by gel electrophoresis and MALDI-MS (FIGS. 9B and 9C) verified conjugation by the Staudinger phosphite reaction (Böhrsch, Hackenberger et al., Chem. Commun. 2010, accepted for publication).

The invention claimed is:

1. A modified macromolecule that has at least one further functional group, comprising at least one x-fold (x≥1) chemoselectively incorporated phosphoramidate group of general formula (I)

—NHPO(OR$^1$)(OR$^{1'}$)     (I)

and/or at least one x-fold (x≥1) chemoselectively incorporated phosphonamide group of general formula (Ia)

—NHPO(R$^1$)(OR$^{1'}$)     (Ia)

wherein R$^1$ and R$^{1'}$ is selected from the group containing glycerol, polyglycerol, PEG polymers of the general empirical formula $C_{2n}H_{4n+2}O_{n+1}$ with n≥1, methyl, ethyl, or butyl; functionalized $C_n$-alkyl chains with n≥1, aryls, heteroaryl, silyl, fluorophores, saccharides, peptides, crown ethers, or a linker, which links the aforementioned groups, and wherein R$^1$ and R$^{1'}$ can be identical to or different from one another, wherein the further functional group in the macromolecule is unprotected.

2. The macromolecule as claimed in claim 1, wherein the number x of incorporated phosphoramidate and/or phosphonic acid groups is between 1 and 50.

3. The macromolecule as claimed in claim 1, wherein the phosphoramidate group of general formula (I) can be converted to a phosphoramide group of general formula (III)

—NHPO(OH)$_2$     (III)

and/or in that the phosphonamide group of general formula (Ia) can be converted to a free phosphonamide group of general formula (IIIa)

—NHP(O)R$^1$(OH).

4. The macromolecule as claimed in claim 1, wherein the macromolecule can be immobilized via the phosphoramidate and/or phosphonamide group on the surface of a support.

5. The macromolecule as claimed in claim 1, wherein polymers, peptides, proteins, glycans, lipids, polynucleotides and/or polyketides are used as the macromolecule.

6. A method of chemoselective phosphorylation of compounds to obtain the modified macromolecule of claim 1, the method comprising the following steps:

a) synthesis and/or functionalization of a compound having at least one functional group with at least one azide (N3) group, and b) reaction of the at least one azide group of the compound:

with a phosphite of general formula (II) P(OR$^1$)(OR$^{1'}$)(OR$^{1''}$) with formation of the phosphoramidate group of general formula (Ia)

NHPO(OR$^1$)(OR$^{1'}$); and/or with a phosphonite of general formula (IIa) PR$^1$ (OR$^{1'}$)(OR$^{1''}$) with formation of the phosphonamide group of general formula (Ia)

NHPO(R$^1$)(OR$^{1'}$), wherein the moieties R$^1$, R$^{1'}$ and R$^{1''}$ are assigned the meaning of R$^1$ and R$^{1'}$.

7. The method as claimed in claim 6, wherein the azide used in step a) has at least one functional group selected from the group containing —OH, —NH$_2$, —SH, —CO$_2$H, —CONH$_2$, disulfides, guanidines, —NHCNHNH$_2$, imidazoles, and indoles.

8. The method as claimed in claim 6, wherein in a step c) following step b), the phosphoramidate group of general formula (I) is reacted to a phosphoramide group of general formula (III) —NHPO(OH)$_2$ and/or the phosphonamide group of general formula (Ia) is reacted to a phosphonamide group of general formula (IIIa) —NHPO(R$^1$)OH.

9. The method as claimed in claim 8, wherein the step of reaction of the phosphoramidate and/or phosphonamide group takes place by photolysis and/or hydrolysis.

10. A method for site-specific immobilization of macromolecules comprising the following steps synthesis or functionalization of a compound having at least one functional group comprising at least one azide (N$_3$) group, wherein a further functional group in the macromolecule is unprotected;

coupling of at least one phosphite of general formula IV P(OR$^2$)(OR$^{2'}$)(OR$^{2''}$) and/or at least one phosphonite of general formula (IVa) PR$^2$ (OR$^{2'}$)(OR$^{2''}$) on the surface of at least one support R$^3$, wherein R$^2$, R$^{2'}$ and R$^{2''}$ are selected from the group containing methyl, ethyl, or butyl, functionalized $C_n$-alkyl chains with n≥1, aryls, heteroaryl, or silyl, wherein R$^2$, R$^{2'}$ and R$^{2''}$ can be identical to or different from one another, and reaction of the at least one azide group of the compound with the at least one support coupled to a phosphite and/or phosphonite, wherein coupling between the support and the compound takes place via a phosphoramidate and/or phosphonamide group and a structure according to —NHPO(OR$^2$)—O—R$^3$ or according to —NHPO(OR$^2$)—R$^3$ is obtained.

11. The method as claimed in claim 10, wherein functionalized glass surfaces, microplates, nanoparticles, in particular gold or silica nanoparticles and quantum dots are used as support $R^3$.

12. A support made by a method as claimed in claim 10 having the structure according to —NHPO($OR^2$)—O—$R^3$ or according to —NHPO($OR^{2'}$)—$R^3$.

* * * * *